US00PP32804P2

(12) United States Plant Patent
Scheffers

(10) Patent No.: US PP32,804 P2
(45) Date of Patent: Feb. 9, 2021

(54) ***DRACAENA* PLANT NAMED 'DRAGREYE'**

(50) Latin Name: *Dracaena fragrans*
Varietal Denomination: DRAGREYE

(71) Applicant: Dragontree Beheer B.V., Honselersdijk (NL)

(72) Inventor: Ruud Scheffers, Honselersdijk (NL)

(73) Assignee: Dragontree Beheer B.V., Honselersdijk (NL)

( * ) Notice: Subject to any disclaimer, the term of this patent is extended or adjusted under 35 U.S.C. 154(b) by 0 days.

(21) Appl. No.: 16/873,493

(22) Filed: Apr. 21, 2020

(51) Int. Cl.
*A01H 5/12* (2018.01)
*A01H 6/12* (2018.01)

(52) U.S. Cl.
USPC ..... Plt./383

(58) Field of Classification Search
USPC ..... Plt./383
CPC ... A01H 5/12; A01H 5/00; A01H 5/02; A01H 6/12; A01H 6/42
See application file for complete search history.

*Primary Examiner* — June Hwu
(74) *Attorney, Agent, or Firm* — Samuel R. McCoy, Jr.

(57) ABSTRACT

A new and distinct *Dracaena* plant named 'DRAGREYE' which is characterized by an abundance of foliage born on an unbranched stem, green foliage with yellow-green axial striations towards the margins, foliage which is narrowly margined yellow, and the stability of these characteristics from generation to generation.

2 Drawing Sheets

Latin name of the genus and species: The Latin name of the genus and species of the novel variety disclosed herein is *Dracaena fragrans.*

Variety denomination: The inventive cultivar of *Dracaena* disclosed herein has been given the variety denomination 'DRAGREYE'.

BACKGROUND OF THE INVENTION

Parentage: 'DRAGREYE' is a spontaneous branch-plant mutation of a *Dracaena fragrans* 'Lemon Surprise' plant (U.S. Plant Pat. No. 12,654) which was discovered at a commercial greenhouse in Honselersdijk, the Netherlands in the spring of 2010. The mutation was initially noted for its abundant foliage with narrow yellow leaf margins. Said mutation was isolated for further evaluation to confirm the uniformity and stability of the unique characteristics first observed. Upon confirmation of the stability and uniformity of the characteristics, the new plant was selected for commercialization.

Asexual Reproduction: Asexual reproduction of 'DRAGREYE' is accomplished by way of rooting stem cuttings. Propagation was first performed in July of 2011 at the inventor's commercial greenhouse in Honselersdijk, the Netherlands. Through eight subsequent generations, the unique features of this cultivar have proven to be stable and true to type.

SUMMARY OF THE INVENTION

The cultivar 'DRAGREYE' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'DRAGREYE'. These characteristics in combination distinguish 'DRAGREYE' as a new and distinct *Dracaena fragrans* cultivar:

1. *Dracaena* 'DRAGREYE' exhibits an abundance of foliage born on an unbranched stem; and
2. *Dracaena* 'DRAGREYE' exhibits green foliage with yellow-green axial striations towards the margins; and
3. *Dracaena* 'DRAGREYE' exhibits foliage which is narrowly margined yellow.

BOTANICAL DESCRIPTION OF THE PLANT

Figure 1:
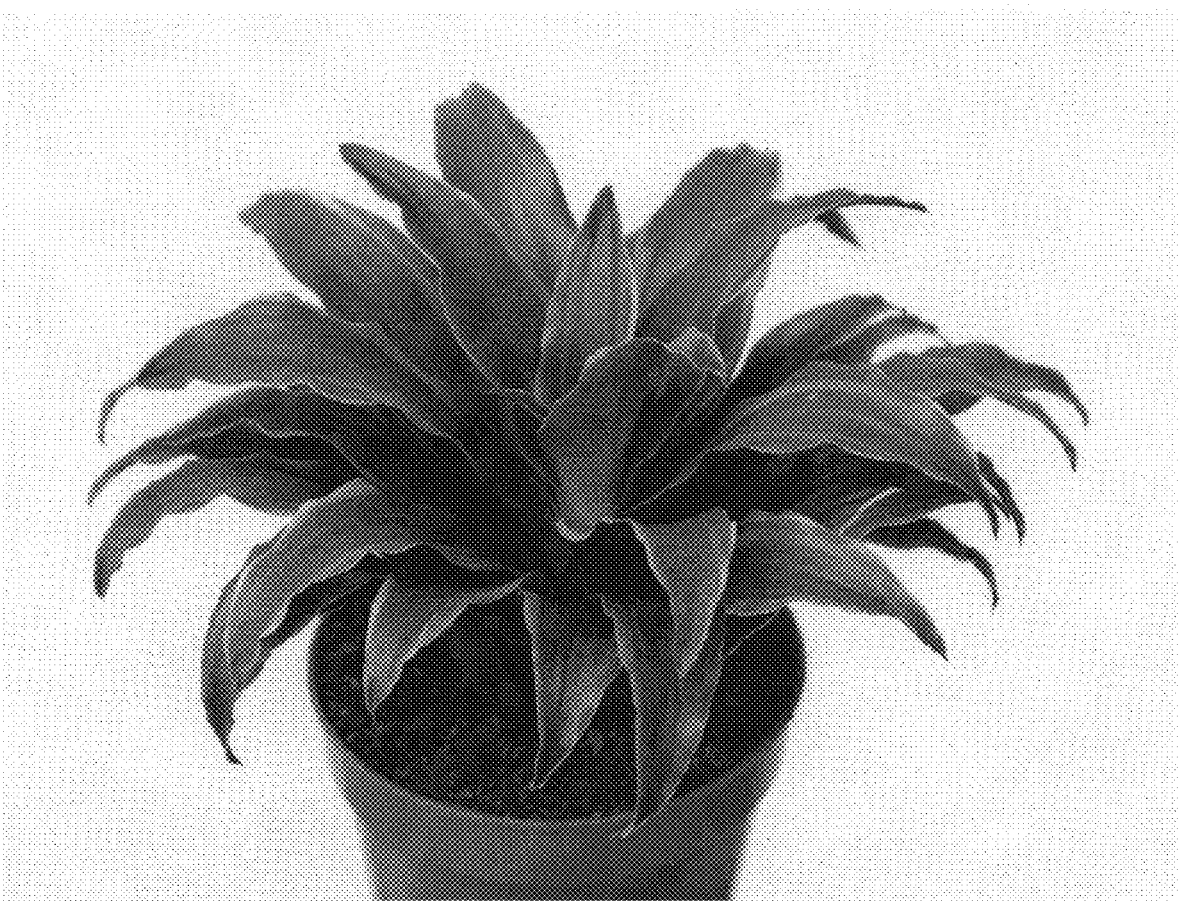
FIG. 1 illustrates, as nearly true as it is reasonably possible to make the same in color photographs of this type, an exemplary plant of 'DRAGREYE' grown in Honselersdijk, the Netherlands. This plant, grown in a 11 cm nursery container, is approximately 16 weeks old from a rooted young plant.
Figure 2:
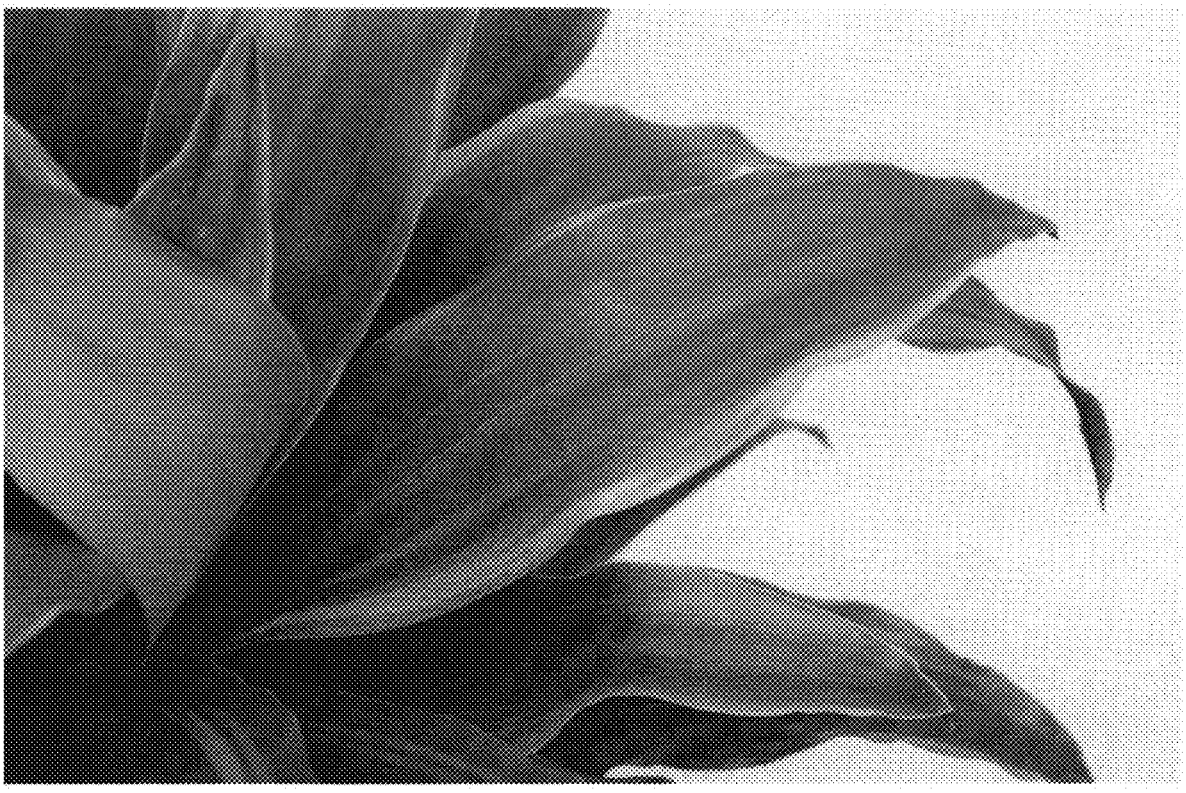
FIG. 2 illustrates, as nearly true as it is reasonably possible to make the same in color photographs of this type, the typical foliage of 'DRAGREYE'.

The following observations and measurements, made in May of 2019, describe averages from a sample set of six specimens of 26 week-old 'DRAGREYE' plants grown in 15 cm nursery pots in San Jose, Costa Rica. Plants were produced using conventional greenhouse production protocols for *Dracaena* sp. which consisted of growing under shade cloth, regular overhead irrigation, and chemical control of thrips insects. No photoperiodic treatments or artificial light was given to the plants.

Those skilled in the art will appreciate that certain characteristics will vary with older or, conversely, with younger plants. 'DRAGREYE' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'DRAGREYE' and comparisons with the parent plant and most similar commercial *Dracaena* cultivar known to the inventor are provided below.

Plant description:

*Growth habit*.—Compact evergreen perennial with foliage born on a solitary short, unbranched stem.

*Plant profile*.—Flattened globular.

*Average height from base to top of foliage*.—14.7 cm.

*Average width*.—Average of 23.4 cm.

*Growth rate*.—Slow growing.

*Plant vigor*.—Moderately vigorous.

*Propagation details*.—Asexual propagation is accomplished by stem cuttings.

*Time to initiate roots*.—Approximately 30 days are required to initiate roots at 20 degrees Celsius.

*Time to produce a marketable* 11 *cm potted plant*.—Approximately 12 to 16 weeks. Pinching will increase lateral branching.

*Disease and pest resistance or susceptibility*.—Neither tolerance nor resistance to normal diseases and pests of *Dracaena fragrans* have been observed.

*Environmental tolerances*.—Adapt to USDA Hardiness Zones 10 through 12 and temperatures as high as 40 degrees Celsius; moderate tolerance to rain and wind.

Root system:

*General*.—Fibrous; freely branched and moderately dense rooting.

*Distribution in the soil profile*.—Shallow to moderately deep.

*Texture*.—Smooth; glabrous.

*Color*.—Greyed-orange, RHS N170A.

Stems:

*Branching characteristics*.—Not freely branched in nature; develops lateral branches only when manipulated by man by way of pruning. Naturally produces one main stem arising from the plant's base.

*Attitude*.—Near vertical.

*Strength*.—Very strong.

*Length*.—5.5 cm.

*Diameter*.—Average 1.2 cm.

*Internode length*.—Average 0.2 cm.

*Stem texture*.—Glabrous; smooth.

*Stem luster*.—Slightly glossy.

*Color, developing stems*.—Green-white, nearest to RHS 157A.

*Color, mature stems*.—Green-white, nearest to RHS 157A.

*Color at the internodes*.—Green-white, nearest to RHS 157A.

Foliage:

*Arrangement*.—Spiraled.

*Attachment*.—Sheathed.

*Division*.—Simple.

*Attitude*.—Foliage near the apex is upright to outward and becomes progressively more relaxed towards the base.

*Number of leaves per lateral branch*.—36.

*Lamina*.—Dimensions — 17.5 cm long and 3.3 cm wide, on average. Shape — Lorate. Aspect — Flat, with the distal most portion on the lamina pointing downward at an average angle of minus-60 degrees to the rest of the lamina. Apex — Acute with a short, soft but pointed tip. Base — Sheathed. Sheath — Length — 1.2 cm. Width — 3.0 cm. Color, adaxial surface — White, nearest to RHS 155A. Color, abaxial surface — White, nearest to RHS 155A. Margin — Entire; light, coarse undulation. Texture and luster of adaxial surface — Smooth, glabrous and moderately glossy. Texture and luster of abaxial surface — Smooth, glabrous and slightly glossy. Color — Juvenile foliage, adaxial surface — Green, nearest to in between RHS NN137A and 137B; narrowly margined and axially striped green, nearest to RHS 143C. Juvenile foliage, abaxial surface — Green, nearest to in between RHS 137B and NN137A, and narrowly margined and axially striped yellow-green, nearest to RHS 145A. Mature foliage, adaxial surface — Green, nearest to a mixture of RHS 137B and NN137A, and narrowly margined and axially striped yellow-green, nearest to RHS 150A. Mature foliage, abaxial surface — Nearest to in between green and yellow-green, RHS 137B and 147B, and narrowly margined and axially striped yellow-green, nearest to in between RHS 150A and 150B. Venation — Pattern — Parallel. Color, adaxial surface — The main vein nearest green, nearest to RHS 143A. All other veins are indistinguishable from the surrounding foliage: green, nearest to in between RHS 137B and NN137A, and narrowly margined and axially striped yellow-green, nearest to RHS 150A. Color, abaxial surface — The main vein is yellow-green, nearest to RHS 144B. All other veins are indistinguishable from the surrounding foliage: nearest to in between green and yellow-green, RHS 137B and 146B, and narrowly margined and axially striped yellow-green, nearest to in between RHS 150A and 150B.

Inflorescence: To date, flowering has not been observed.

Flower buds: To date, flowering has not been observed.

Flower: To date, flowering has not been observed.

Reproductive organs: To date, flowering has not been observed.

Seed and fruit: To date, flowering has not been observed.

COMPARISONS WITH THE PARENT PLANT

Plants of the new cultivar 'DRAGREYE' may be distinguished from its parent, *Dracaena fragrans* 'Lemon Surprise', by the characteristics described in Table 1.

TABLE 1

| Characteristic | 'DRAGREYE' | 'Lemon Surprise' |
|---|---|---|
| Abundance of foliage. | More abundant than 'Steudneri'. | Less abundant than 'DRAGREYE'. |
| Foliage length. | Shorter than 'Steudneri'. | Longer than 'DRAGREYE'. |
| Foliage aspect. | Flat and curled downward distally. | Slightly spiralled. |
| Base color of the foliage. | Uniformly green. | Varying shades of green. |
| Variegation of the foliage. | No white striping. | Axially striped white. |
| Foliage margin coloration. | Narrowly margined yellow. | Broadly margined in between light green and yellow. |

Plants of the new cultivar 'DRAGREYE' may be distinguished from the closest known commercial comparator,

*Dracaena fragrans* 'Janet Craig' (not patented), by the characteristics described in Table 2.

TABLE 2

| Characteristic | 'DRAGREYE' | 'Janet Craig' |
|---|---|---|
| Abundance of foliage. | More abundant than 'Janet Craig'. | Less abundant than 'DRAGREYE'. |
| Foliage attitude. | Foliage is generally more relaxed. | Foliage is generally more upright. |
| General coloration of the foliage. | Darker shade of green. | Lighter shade of green. |

TABLE 2-continued

| Characteristic | 'DRAGREYE' | 'Janet Craig' |
|---|---|---|
| Foliage margin coloration. | Narrowly margined yellow. | Not margined yellow. |

That which is claimed is:

1. A new and distinct cultivar of *Dracaena* plant named 'DRAGREYE', substantially as described and illustrated herein.

* * * * *